(12) United States Patent
Ghosh et al.

(10) Patent No.: US 12,740,715 B2
(45) Date of Patent: Sep. 22, 2026

(54) WEARABLE DEVICE, SYSTEM AND METHOD FOR MONITORING CARDIAC FUNCTION/STRESS DURING APNOEIC EPISODE

(71) Applicant: Turtle Shell Technologies Private Limited, Bengaluru (IN)

(72) Inventors: Abin Ghosh, Bengaluru (IN); Tejashri Varur, Bengaluru (IN); Umesh Mohan, Bengaluru (IN)

(73) Assignee: Turtle Shell Technologies Private Limited, Bengaluru (IN)

( * ) Notice: Subject to any disclaimer, the term of this patent is extended or adjusted under 35 U.S.C. 154(b) by 0 days.

(21) Appl. No.: 19/370,966

(22) Filed: Oct. 28, 2025

(65) Prior Publication Data

US 2026/0047767 A1 Feb. 19, 2026

(30) Foreign Application Priority Data

Jun. 19, 2025 (IN) ............................ 202541058940

(51) Int. Cl.
*A61B 5/318* (2021.01)
*A61B 5/00* (2006.01)
(Continued)

(52) U.S. Cl.
CPC .......... *A61B 5/0205* (2013.01); *A61B 5/1102* (2013.01); *A61B 5/33* (2021.01);
(Continued)

(58) Field of Classification Search
CPC ....... A61B 5/0205; A61B 5/1102; A61B 5/33; A61B 5/4561; A61B 5/4818;
(Continued)

(56) References Cited

U.S. PATENT DOCUMENTS

2004/0254483 A1* 12/2004 Zdeblick ............ A61B 5/02158 600/486
2012/0109243 A1* 5/2012 Hettrick ................ A61B 5/686 600/509

(Continued)

FOREIGN PATENT DOCUMENTS

AU 2017200083 B2 2/2017
CN 105208921 A 12/2015

(Continued)

*Primary Examiner* — Niketa Patel
*Assistant Examiner* — Karmel J Webster
(74) *Attorney, Agent, or Firm* — Jason A. Smith; Shumaker, Loop & Kendrick, LLP

(57) ABSTRACT

A wearable device (100) for monitoring cardiac function during apnoeic episode. Wearable device including ballistocardiography (BCG) sensor (102A) to measure mechanical forces generated by heart and respiratory movement; electrocardiography (ECG) sensor (102B) to measure electrical activity of heart; and processor (102C) operatively connected to BCG sensor and ECG sensor to generate BCG data from measured mechanical forces and ECG data from measured electrical activity, respectively. Processor configured to: filter respiratory signals and heart signals from BCG data; detect apnoeic episode based on low respiratory signals or absence of respiratory signals for predetermined time period in filtered BCG data; determine compensatory mechanical output of heart using at least one of filtered BCG data or ECG data for apnoeic episode, and predict risk of cardiac condition based on compensatory mechanical output during apnoeic episode. Also a system (300) and method thereof.

20 Claims, 4 Drawing Sheets

(51) Int. Cl.

*A61B 5/0205* (2006.01)
*A61B 5/11* (2006.01)
*A61B 5/33* (2021.01)
*A61B 5/024* (2006.01)
*A61B 5/08* (2006.01)

(52) U.S. Cl.

CPC .......... *A61B 5/4561* (2013.01); *A61B 5/4818* (2013.01); *A61B 5/6801* (2013.01); *A61B 5/7225* (2013.01); *A61B 5/7275* (2013.01); *A61B 5/746* (2013.01); *A61B 5/02405* (2013.01); *A61B 5/02416* (2013.01); *A61B 5/02438* (2013.01); *A61B 5/0816* (2013.01); *A61B 2562/0219* (2013.01)

(58) Field of Classification Search

CPC ... A61B 5/6801; A61B 5/7225; A61B 5/7275; A61B 5/746; A61B 5/02405; A61B 5/02416; A61B 5/02438; A61B 5/0816; A61B 2562/0219

See application file for complete search history.

(56) References Cited

U.S. PATENT DOCUMENTS

2015/0257680 A1* 9/2015 Inan .................... A61B 5/0205 600/301
2017/0164840 A1* 6/2017 Matsumoto ........ A61B 5/14542
2017/0238815 A1* 8/2017 Luxon ................ A61B 5/02055
2018/0020931 A1* 1/2018 Shusterman ......... A61N 1/3627 600/483
2019/0314192 A1* 10/2019 Raj ...................... A61B 5/0002
2019/0358464 A1* 11/2019 Volosin ................ A61B 5/0205
2021/0369191 A1* 12/2021 Gill ........................ A61B 5/389
2023/0337937 A1* 10/2023 Barlow ................ A61B 5/0826
2024/0350076 A1* 10/2024 Tzeng .................... G16H 40/67

FOREIGN PATENT DOCUMENTS

EP 2854636 B1 8/2019
WO WO-2017212370 A1 * 12/2017 ........... A61B 5/7278

* cited by examiner

WEARABLE DEVICE, SYSTEM AND METHOD FOR MONITORING CARDIAC FUNCTION/STRESS DURING APNOEIC EPISODE

PRIORITY INFORMATION

The present application claims priority from Indian Patent Application number 202541058940 filed on 19 Jun. 2025.

FIELD OF THE INVENTION

The present disclosure relates to a wearable device for monitoring cardiac function during an apnoeic episode. Moreover, the present disclosure also relates to a system for monitoring cardiac function during an apnoeic episode. Furthermore, the present disclosure relates to a method for monitoring cardiac function during an apnoeic episode.

BACKGROUND OF THE INVENTION

Sleep apnoea is a condition that affects breathing during sleep, characterized by repeated interruptions in breathing, known as apnoeic episodes, where airflow stops and restarts. The apnoeic episodes typically last at least 10 seconds and occur frequently throughout sleep, reducing oxygen supply to the body. The sleep apnea is strongly associated with an increased risk of cardiovascular diseases, including high blood pressure, stroke, and coronary artery disease. In particular, obstructive sleep apnoea has been linked to left ventricular diastolic dysfunction, which contributes to heart failure risk. Thus, monitoring cardiac function during sleep is critical for assessing the cardiovascular impact of the sleep apnoea and for managing associated health risks. Conventionally, cardiac activity is measured using electrocardiography which records electrical signals, and echocardiography. In clinical settings, invasive techniques such as catheterization provide detailed hemodynamic measurements, including intracardiac pressure and cardiac output.

While conventional methods provide valuable insights, they are often restricted to clinical environments, require specialized equipment, and may cause patient discomfort, limiting their feasibility for long-term and continuous monitoring. The PSG and other hospital-based assessments remain expensive, cumbersome, and impractical for routine home-based cardiac monitoring during sleep. The lack of a non-invasive, integrated solution capable of simultaneously evaluating sleep apnoea, cardiac function, and associated cardiovascular stress highlights the need for an advanced monitoring approach.

Therefore, in the light of foregoing discussion, there exists a need to overcome the aforementioned drawbacks.

SUMMARY OF THE INVENTION

A primary objective of the present disclosure seeks to provide a wearable device for monitoring cardiac function during an apnoeic episode. The wearable device comprises a ballistocardiography (BCG) sensor configured to measure mechanical forces generated by a heart and respiratory movement, and an electrocardiography sensor configured to measure electrical activity of the heart, ensuring comprehensive monitoring of cardiac function. Notably, the wearable device includes a processor operatively connected to the BCG sensor and the ECG sensor to generate BCG data and ECG data, respectively, allowing for real-time processing and analysis of cardiac and respiratory signals.

Another objective of the present disclosure seeks to provide a method for detecting an apnoeic episode based on low respiratory signals or absence of respiratory signals for a predetermined time period in the filtered BCG data, thereby facilitating early and reliable detection of apnoeic episodes.

Yet another objective of the present disclosure seeks to provide a system for monitoring cardiac function during the apnoeic episode that enables early detection of cardiac risks associated with apnoeic episodes, allowing timely medical intervention.

An aim of the present disclosure is to provide a solution for predicting a risk of a cardiac condition based on compensatory mechanical output during the apnoeic episode. By analyzing the cardiac response during the apnoeic episode, the wearable device facilitates risk assessment for cardiac conditions, including heart failure, thereby enabling early medical intervention. The wearable device provides continuous monitoring solutions, overcoming at least partially the limitations associated with clinical diagnostic methods such as polysomnography.

In a first aspect, an embodiment of the present disclosure provides a wearable device for monitoring cardiac function during an apnoeic episode, the wearable device comprising:

a ballistocardiography (BCG) sensor configured to measure mechanical forces generated by a heart and respiratory movement;

an electrocardiography sensor configured to measure electrical activity of the heart; and a processor operatively connected to the BCG sensor and the ECG sensor to generate BCG data from the measured mechanical forces and ECG data from the measured electrical activity, respectively, the processor is configured to:

filter respiratory signals and heart signals from the BCG data;

detect the apnoeic episode based on low respiratory signals or absence of respiratory signals for a predetermined time period in the filtered BCG data;

determine a compensatory mechanical output of the heart using at least one of the filtered BCG data or ECG data for the apnoeic episode, and predict a risk of a cardiac condition based on the compensatory mechanical output during the apnoeic episode.

Advantageously, the aforementioned wearable device provides accurate information on possible cardiac condition of the user based on the compensatory mechanical output measured during the apnoeic episode. In this regard, the aforementioned wearable device utilizes derivatives from BCG data, such as heart rate, respiration rate, compensatory mechanical output, and variations in intrathoracic pressure, to provide a comprehensive and reliable analysis of cardiac function during apnoeic episodes, which can provide accurate insight into functionality of cardiorespiratory system of user and can detect possible cardiac condition of the user. Additionally, the wearable device is equipped with remote monitoring facility enabling early detection of health issues (cardiac condition), within comfort of home while reducing cost of such monitoring in a clinical setting.

In a second aspect, an embodiment of the present disclosure provides a system for monitoring cardiac function during an apnoeic episode, the system comprising:

a wearable device configured to be worn on a chest near a sternum of a user, the wearable device comprising:

a ballistocardiography (BCG) sensor configured to measure mechanical forces generated by a heart;

an electrocardiography sensor configured to measure electrical activity of the heart; and a processor operatively connected to the BCG sensor and the ECG sensor to generate BCG data from the measured mechanical forces and ECG data from the measured electrical activity, respectively;

and a server arrangement communicably coupled to the wearable device for receiving the BCG data and the ECG data, the server arrangement is configured to:

filter respiratory signals and heart signals from the BCG data;

detect the apnoeic episode based on low respiratory signals or absence of respiratory signals for a predetermined time period in the filtered BCG data;

determine a compensatory mechanical output of the heart using at least one of the filtered BCG data or ECG data for the apnoeic episode; and predict a risk of a cardiac condition based on the compensatory mechanical output during the apnoeic episode.

The system is configured to correlate various measured vitals (such as BCG signal derivatives received from the wearable device, ECG signals from an external sensor and so on) and accurately detect cardiac condition of the user therefrom. Moreover, the system is configured to detect whether the apnoeic episode is a central apnoea or obstructive sleep apnoea, to provide a quantitative assessment of cardiac risk associated with apnoea-induced stress. Moreover, advantageously, the system is configured to detect and predict the likelihood of the cardiac condition based on long-term variations in cardiac failure risk indices, enabling early intervention and improved health outcomes. Furthermore, the system comprises a server arrangement with advanced processing capabilities, allowing for automated data analysis, risk prediction, and remote monitoring. Additionally, the system is configured to integrate data received on various vitals from external sensors such as a PPG sensor and an inertial measurement unit (IMU), in order to further refine the detection of apnoeic episodes by analyzing blood oxygen saturation levels and sleep posture correlations, respectively.

In a third aspect, an embodiment of the present disclosure provides a method for monitoring cardiac function during an apnoeic episode, the method comprising:

measuring mechanical forces generated by a heart using a ballistocardiography (BCG) sensor;

measuring electrical activity of the heart using an electrocardiography sensor;

generating BCG data from the measured mechanical forces and ECG data from the measured electrical activity using a processor;

filtering respiratory signals and heart signals from the BCG data;

detecting the apnoeic episode based on low respiratory signals or absence of respiratory signals for a predetermined time period in the filtered BCG data;

determining a compensatory mechanical output of the heart using at least one of the filtered BCG data or ECG data for the apnoeic episode; and predicting a risk of a cardiac condition based on the compensatory mechanical output during the apnoeic episode.

The aforementioned method aids in continuous monitoring of a user's cardiorespiratory health. Beneficially, the aforementioned method aid in the integration of continuously measured vitals (such as mechanical forces generated by the heart, respiratory movement from BCG data, and electrical activity of the heart from ECG data) to monitor cardiac function during an apnoeic episode and to determine the cardiac condition of the user based on the measured vitals. Therefore, continuous and non-intrusive health monitoring is achieved, enhancing user comfort and facilitating real-time assessment of cardiac stress and apnoea-induced physiological changes.

Embodiments of the present disclosure substantially eliminate or at least partially address the limitations of existing monitoring systems by providing a more accurate and predictive approach to assessing cardiac function during apnoeic episodes. As a result, the system minimizes the risks associated with undetected apnoea-induced cardiac stress and enhances the ability to provide timely medical intervention.

Additional aspects, advantages, features, and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of embodiments, is better understood when read in conjunction with the appended drawings. For the purpose of illustrating the present disclosure, exemplary constructions of the disclosure are shown in the drawings. However, the present disclosure is not limited to specific instrumentalities disclosed herein. Moreover, those skilled in the art will understand that the drawings are not to scale.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

Figure 1:
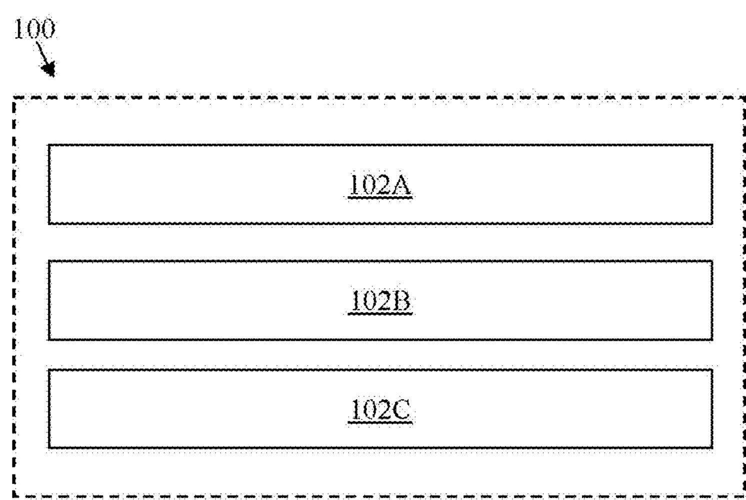
FIG. 1 illustrates a block diagram of depicting components of a wearable device for monitoring cardiac function during an apnoeic episode, in accordance with an embodiment of the present disclosure.

Referring to FIG. 1, illustrated is a wearable device 100 for monitoring cardiac function during an apnoeic episode, in accordance with an embodiment of present disclosure. As shown, the wearable device 100 comprises a ballistocardiography (BCG) sensor 102A, an electrocardiography sensor 102B and a processor 102C operatively connected to the BCG sensor 102A and the ECG sensor 102B. In this regard, throughout the present disclosure, the term "apnoeic episode" refers to an involuntary pause, cessation in breathing, that can occur in various conditions, including sleep or state of semiconsciousness. In other words, Herein, the apnoeic episode refers to an event characterized by a temporary cessation of breathing during sleep, which disrupts normal respiratory function and affects oxygen supply to the user's body. In this regard, throughout the present disclosure, the term "wearable device" refers to body-worn electronic device or an apparatus configured to monitor cardiac function during the apnoeic episode. The wearable device 100 may be worn by a user in proximity to the chest region to facilitate the accurate capture of signals associated with cardiac function and respiratory movement. For example, the wearable device 100 may be attached and/or worn nearby sternum of the user. Notably, the term "user" as used herein refers to a person, an animal, who may be a person, a patient or a test subject undergoing a clinical assessment, or who requires monitoring specifically during sleep state. It may be appreciated that the wearable device 100 is intended for continuous and non-invasive (or minimal invasive) monitoring of cardiac function, particularly during sleep. In this regard, it may be appreciated that the wearable device 100 may be implemented by embodying in various form factors, including but not limited to a chest straps, smart clothing (integrated with textile-based sensors), and patches or adhesive devices. The wearable device is specifically intended to assess cardiac stress during apnoeic episodes. It may also be appreciated that the wearable device 100 is designed for application in home-based and clinical settings, offering a practical alternative to conventional cardiac monitoring methods that require hospital-based equipment.

Throughout the present disclosure, the term "cardiac function" refers to physiological function or activity performed by the heart. For example, the cardiac function may include pumping blood, heartbeat, and similar functions associated with the heart. The cardiac function may be monitored by utilising sensors raging from the BCG sensor 102A, the ECG sensors 102B and the like. It may be appreciated that cardiac function is affected by respiratory activities/movement of the user's lungs (for supplying oxygen to blood pumped by the heart), and therefore the while monitoring the cardiac function, generated data (such as BCG waveforms) also comprise information related to respiratory activities/movement.

Notably, the BCG sensor 102A of the wearable device 100 is configured to measure mechanical forces generated by a heart and respiratory movement. In this regard, the BCG sensor 102A is a sensing element/component configured to measure mechanical forces generated by the heart and respiratory movements. The BCG sensor utilizes a non-invasive technique that detects subtle body movements caused by ballistic forces of blood ejection from the heart into vascular system. The BCG sensor 102A operates by capturing the mechanical forces. The BCG sensor 102A is integrated into the wearable device 100 and is positioned near the chest area to detect micro-scale body movement caused by cardiac contractions. These mechanical signals are recorded as BCG waveform data, which provides insight into the cardiac function, including heart contractility, cardiac output, and an impact of respiratory movement on the performance of the heart.

Notably, the ECG sensor 102B of the wearable device 100 configured to measure electrical activity of the heart. In this regard, the ECG sensor 102B is designed to detect bioelectrical signals generated by the heart. The ECG sensor 102B functions by detecting bioelectrical signals generated by the heart as it undergoes depolarization and repolarization during each cardiac cycle. The ECG sensor 102B operates by utilizing surface electrodes placed on the skin, typically near the chest area when integrated into the wearable device 100. These electrodes detect and/or measure electrical activity (small voltage changes) that occur due to the propagation of electrical impulses through the heart.

Further, the processor 102C (operatively coupled to the BCG sensor 102A and the ECG sensor 102B) is configured to generate BCG data from the measured mechanical forces and ECG data from the measured electrical activity, respectively. The processor 102C is further configured to filter respiratory signals and heart signals from the BCG data; detect the apnoeic episode based on low respiratory signals or absence of respiratory signals for a predetermined time period in the filtered BCG data; determine a compensatory mechanical output of the heart using at least one of the filtered BCG data or ECG data for the apnoeic episode, and predict a risk of a cardiac condition based on the compensatory mechanical output during the apnoeic episode.

It may be appreciated that the term "processor" as used herein refers to a micro-controller, a micro-processor, an on-chip-processor, and so on which is capable of receiving input (i.e., BCG and ECG data), analyze the received input, and provide an output (i.e., determination of cardiac condition). The BCG data refers to the signal representing mechanical movement and displacement of body caused by the mechanical forces generated during each cardiac cycle and respiratory activity. Notably, the BCG data typically exhibits distinct peaks corresponding to cardiac events. For example, the BCG data includes information on various signal forms such as I, J, K, L, M, N waves which corresponds to various cardiac activities and key peaks linked to systolic and diastolic phases. The mechanical movement occur as a result of blood ejection from the heart into pulmonary (respiratory) and circulatory system of the user's body, along with respiratory-induced thoracic movements. Thus, the BCG data includes heart signals as well as respiratory signals, collected as a time-series waveform that reflects the mechanical aspects of cardiac function, including heart contractility, cardiac output, and vascular compliance.

Herein, the processor 102C is configured to filter the respiratory signals and the heart signals from the BCG data. The processor 102C is configured to apply suitable filtering techniques to the BCG data to filter out noise, separate cardiac and respiratory components, and detect deviations indicative of an apnoeic episode. In this regard, such suitable filtering techniques comprises at least one of: bandpass filter, notch filter, median filter, least mean squares (LMS) filter, recursive least squares (RLS) filter, empirical mode decomposition (EMD), independent component analysis (ICA), Savitzky-Golay filter and so on. Notably, the processor 102C is configured to apply the suitable filtering technique based on the volume of BCG data available. The BCG data is further analysed to assess a compensatory mechanical output of the heart, allowing for the evaluation of cardiac stress during sleep-related breathing disturbances. In addition to that, the processor 102C is configured to receive the ECG data (i.e., electrical signals associated with the heart's rhythmic contractions), as recorded, from the ECG sensor 102B. The ECG data is continuously monitored to detect abnormalities that may indicate underlying cardiac stress during the apnoeic episode.

The processor 102C is configured to determine the compensatory mechanical output of the heart by using least one of the filtered BCG data or ECG data obtained during, before and after the apnoeic episode. Notably, the term "compensatory mechanical output" refers to the heart's adaptive mechanical response to maintain adequate blood flow when faced with stress, or dysfunction during an apnoeic episode, in order to preserve blood flow volume and blood oxygen saturation. It may be appreciated that cardiac output (the amount of blood ejected by the left ventricle of the heart into the aorta per unit of time) is varied based to maintain adequate blood circulation (i.e., blood flow volume) and blood oxygen saturation.

Moreover, the processor 102C is configured to detect the apnoeic episode based on low respiratory signals or absence of respiratory signals for a predetermined time period in the filtered BCG data. In this regard, low respiratory signal refers to respiratory signal with significantly low amplitude value indicating that respiration activities are compromised. Notably, the respiratory signal provide insight on depth and duration of respiratory activities and analysis thereof provide insight on an apnoeic episode, duration of apnoeic episode and so on. In this regard, the processor 102C evaluates and corelates occurrence of the apnoeic episodes by assessing their duration, frequency, and impact on cardiac function. If the respiratory signals amplitude falls below the predefined threshold or ceases altogether for the predetermined time period, the processor 102C determines that the apnoeic episode has occurred. Herein, the term "predetermined time period" refers to a time duration for which breathing stops or significantly reduced to qualify as the apnoeic episode. For example, the predetermined time period may be at least 10 seconds. In this regard, absence of respiration for a duration of 10 seconds or more is considered an apnoeic episode. However, the predetermined time period may vary based on configurable thresholds or user-specific physiological parameters, allowing for adaptive detection tailored to individual health conditions. The processor 102C is configured to apply these criteria to differentiate between brief pauses in breathing and the apnoeic episode that are clinically significant, ensuring accurate identification and assessment of sleep-related breathing disturbances.

In particular, the processor 102C utilizes the BCG data to detect the apnoeic episode based on reduced or absent respiratory-induced vibrations for the predetermined time period. Additionally, the BCG sensor 102A works in conjunction with the ECG sensor 102B to provide a comprehensive assessment of cardiac responses during sleep, enabling early detection of changes in mechanical heart function due to the apnoeic episode. During the apnoeic episode, the absence of airflow leads to a compensatory response from the cardiovascular system, increasing the workload on the heart.

Further, the processor is configured to determine the compensatory mechanical output of the heart using at least one of: the filtered BCG data or ECG data for the apnoeic episode. In this regard, when breathing ceases temporarily, specifically, due to the apnoeic episode, the user's body experiences reduced oxygen intake and increased physiological stress, prompting the heart to compensate by altering its mechanical function. This compensation may include changes in stroke volume, contractility, heart rate, or force of cardiac contractions. The processor 102C analyses the filtered BCG data, and the ECG data, to determine the compensatory mechanical output. For example, the heart may pump blood more rapidly than normal pumping to maintain required blood flow and blood oxygen saturation level throughout the body, thus increasing the heart rate, the stroke volume, the contractility and other mechanical aspect of cardiac activities. Analysis of changes in such mechanical aspects can provide reliable information on cardiac functionality and cardiac health. Furthermore, the processor 102C is configured to predict a risk of a cardiac condition based on the compensatory mechanical output during the apnoeic episode. Notably, the term "cardiac condition" as used herein refers to any physiological condition that puts stress on the heart and can cause heart disease. It may be appreciated that the wearable device 100 is configured to corelated the compensatory mechanical output (determined from measured the BCG data and ECG data) with possible cardiac condition thereby providing early detection facility for improved health monitoring. Herein, the processor 102C may predict a level or chance of cardiac failure based on the cardiac condition of the heart. For example, if a user having frequent apnoeic episodes, then the cardiac activities and cardiac health may be compromised. Notably, the condition (health) of the heart can be assessed based on how the heart is responding under frequent apnoeic episodes. Based on such information (i.e., how the heart is responding under frequent apnoeic episodes), the processor 102C can predict whether the user is prone to a greater risk of possible cardiac condition in comparison to another user having less frequency of apnoeic episodes.

Figure 2:
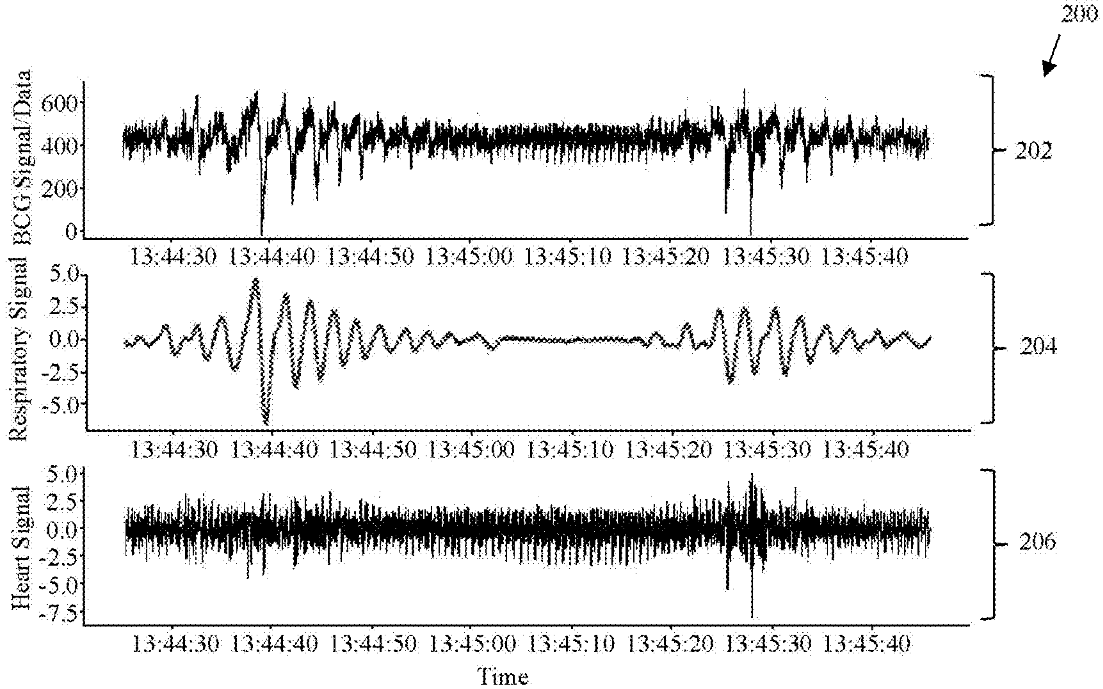
FIG. 2 illustrates a graphical representation of ballistocardiography (BCG) data received from a ballistocardiography (BCG) sensor, in accordance with an embodiment of the present disclosure.

Referring to FIG. 2, illustrated is a graphical representation 200 of BCG data 202 received from a ballistocardiography (BCG) sensor (namely, BCG sensor 102A), in accordance with an embodiment of the present disclosure. The illustrated graphical representation 200 provides a visualization of the physiological variations observed during the apnoeic episode. As shown, the BCG data 202 provides a combined representation of mechanical forces generated by cardiac and respiratory activity, which can be further decomposed into its respective respiratory and heart signal components for a detailed analysis of the subject's cardiovascular response to the apnoeic episode. As seen in FIG. 2, the BCG data 202 is segregated into a respiratory signal 204 representing the breathing related signal of the user and a heart signal 206 representing mechanical output of the heart of the user. As observed from the graphical representation, the respiratory signal 204 shows a flatline pattern for certain time interval (i.e., from time 13:45:00 to time 13:45:20) indicating absence of breathing during the said time interval, and the occurrence of the apnoeic episode. Concurrently, in the heart signal 206, the peaks progressively enlarge during the time interval 13:45:00 to 13:45:20, or after the duration of the apnoeic episode reflecting compensatory mechanism (represented as compensatory mechanical output throughout the present disclosure) of the heart in response to cardiac stress or apnoea-induced stress in order to maintain adequate circulation despite the absence of normal respiratory function.

In an embodiment, the processor is configured to determine the compensatory mechanical output using the filtered BCG data by:

determining a stroke volume by calculating area under curve between peaks of the heart signals of the filtered BCG data before, during and after the apnoeic episode;

identifying the stroke volume corresponding to increased peak-to-peak amplitude changes in the heart signals during the apnoeic episode; and calculating a cardiac output as a product of a heart rate determined from the ECG data after the apnoeic episode and the identified stroke volume after the apnoeic episode.

In this regard, the term "stroke volume (SV)" refers to refers to the amount of blood ejected by the left ventricle of the heart during each contraction (systole). Notably, stroke volume is considered to be a key parameter for assessing cardiac performance and circulatory efficiency. The mathematical formula for calculating stroke volume is given below:

$$SV = EDV - ESV$$

wherein end-diastolic volume (EDV) is a volume of blood in the ventricle at the end of diastole (just before contraction), end-systolic volume (ESV) is a volume of blood remaining in the ventricle after systole (after contraction). Notably, the stroke volume of a healthy user without cardiac condition is 60-100 mL per beat which may vary depending on the physiological conditions, height, weight, age, athletic activities, and so on. When the apnoeic episode occurs, the cessation or reduction of breathing leads to decreased oxygen levels and increased cardiovascular stress. Correspondingly, various waveform components and their peaks (i.e., amplitudes) changes. For example, the area under curve of the BCG data changes. Notably the area under the curve is calculated between the I-wave and L-wave extremums (peaks) to provide accurate estimation of stroke volume. Additionally, the amplitude of the J-wave in the heart signal component of the filtered BCG data, may also be utilized to determine the stroke volume corresponding to increased peak-to-peak amplitude changes in the heart signals during the apnoeic episode. Notably, the J-wave represents the recoil forces from the ejection of blood from the ventricles, I-wave is linked to the isovolumetric contraction phase, where the ventricles contract without blood ejection yet, and L-wave is associated with the recoil effect as blood flows through the vascular system and the heart transitions to the relaxation phase. The BCG data may also comprise h-wave is associated with the atrial contraction phase, and k-wave corresponds to the recoil effect following peak blood ejection. The heart compensates for the cardiovascular stress by altering its mechanical functions, which may involve increased stroke volume, changes in contractility, and modifications in heart rate. The alteration in mechanical functions is reflected in the BCG data as variations in the mechanical forces generated by the heart. The processor 102C analyses the alteration to quantify the compensatory mechanical output (compensatory response) of the heart based on the filtered BCG data.

Moreover, the processor 102C determines the stroke volume by calculating area under curve between peaks of the heart signals of the filtered BCG before, during, and after the apnoeic episode. Notably, the BCG data includes mechanical vibrations caused by the ejection of blood by the heart, and therefore area under curve of the filtered BCG data (specifically, the heart signals component of the BCG data) between the peaks of I and L-waves, as well as variations in the peak-to-peak amplitude of J-wave of the heart signals correspond to changes in stroke volume. In this regard, the term "peak-to-peak amplitude changes" refers to variations in the maximum and minimum signal amplitudes recorded in the BCG data (receive in from of a waveform) over successive cardiac cycles. These changes are indicative of fluctuations in the force of cardiac contractions, which, in turn, influence the volume of blood ejected by the heart. The processor 102C evaluates the area under curve between the peaks of the I-wave and L-wave, and corelates the evaluated area under curve with the peak-to-peak amplitude changes in J-wave at different time intervals, for example, before, during, and after the apnoeic episode, to assess how the stroke volume is affected by respiratory cessation and subsequent recovery.

Further, the processor 102C identifies the stroke volume from the area under curve between the peaks of the heart signals after the apnoeic episode. After the apnoeic episode, the body typically exhibits a compensatory response, which may include an increase in stroke volume to restore oxygen delivery to tissues. The processor 102C detects the changes in the area under curve and associates it with a corresponding rise in stroke volume, providing a quantitative measure of the heart's compensatory adjustment following the apnoeic episode.

Furthermore, the processor 102C calculates the cardiac output as a product of a heart rate determined from the ECG data after the apnoeic episode and the identified stroke volume after the apnoeic episode. In this regard, the term "cardiac output (CO)" refers to the total volume of blood pumped by the heart per minute, which is calculated as the product of the stroke volume and the heart rate associated with the heart from the ECG data. The ECG data provides precise heart rate measurements by capturing the electrical impulses that regulate cardiac cycles. By multiplying post-apnoeic episode heart rate (i.e., heart rate after the apnoeic episode) with the identified stroke volume, the processor 102C determines the cardiac output, enabling an assessment of how effectively the heart is compensating for the apnoeic episode. The technical effect is accurate assessment of cardiac condition of the user.

In an embodiment, the processor is configured to predict the risk of the cardiac condition as a current cardiac failure risk-index, calculated using a cardiac index, which is the cardiac output adjusted for body surface area. In this regard, the term "current cardiac failure risk-index" refers to real time cardiac failure risk of the heart. In particular the current cardiac failure risk-index is a quantitative measure that assesses the likelihood of an individual experiencing a cardiac condition based on physiological parameters derived from the cardiac function. Notably, the current cardiac failure risk-index is calculated using the cardiac index, which represents the cardiac output adjusted for the body surface area of the individual, ensuring a more personalized and accurate assessment of cardiac performance relative to body size. The cardiac index is determined using the formula:

$$\text{Cardiac Index} = [\text{Cardiac Output } (CO)]/[\text{Body Surface Area } (BSA)]$$

where the cardiac output refers to the total volume of blood the heart pumps per minute, and the BSA represents a total surface area of the body of the individual, typically calculated using established formulas such as DuBois & DuBois method.

To determine the current cardiac failure risk-index, the processor 102C evaluates the cardiac index in real-time, analyzing deviations from normal physiological ranges. When the cardiac index drops below a threshold value of 2.2 L/min/$m^2$ during the apnoeic episode, it serves as a critical indicator of inadequate cardiac output, prompting an alert generation to notify the user or healthcare provider of a potential cardiac risk. This threshold is based on clinical standards that define low cardiac index as indicative of cardiogenic shock or heart failure, where the heart is unable to pump enough blood to meet the body's metabolic demands. For instance, if a patient's cardiac index is consistently observed near or below 2.2 L/min/$m^2$ across multiple apnoeic episodes, it may suggest a progressive decline in heart function. The processor 102C may utilize historical data (stored in a data repository which may be a local data repository such as a memory chip, a hard drive, a pen drive, and so on or a cloud-based data repository, communicably coupled the processor 102C) to identify whether the cardiac index is trending downward over time, signalling an increasing risk of cardiac decompensation. For example, the historic data may be BCG data stored in the data repository comprising once-a-week overnight recording performed over a period of a month or more. Conversely, if the cardiac index remains within a safe range (typically 2.5-4.0 L/min/$m^2$), the processor 102C may determine that no immediate risk is present.

Notably, the progression cardiac failure risk index is generated by quantifying percentage increase in the cardiac index during apnoeic episodes relative to a baseline cardiac index measured during non-apnoeic periods, measuring a recovery time for the cardiac index to return to the baseline cardiac index after each apnoeic episode, analyzing trends in the quantified percentage increase in cardiac index and the measured recovery time over multiple apnoeic episodes throughout a sleep cycle; and comparing the percentage increase, the recovery time, and the analysed trends to predefined thresholds for cardiac output and recovery time metrics to categorize the cardiac risk level. In this regard, the baseline cardiac index refers to a nominal value when the heart capacity is not compromised. For example, the baseline cardiac index ranges from 2.5 to 4.0 L/min/$m^2$ for a healthy human. A low cardiac index (<2.2 L/min/$m^2$) suggests inadequate cardiac output, often seen in heart failure or shock and a high cardiac index (>4.0 L/min/$m^2$) can be due to hyperdynamic circulation (e.g., sepsis, anaemia, hyperthyroidism). The technical effect is quantization of cardiac condition of the user, for ease of alert generation and administering healthcare provision.

In an embodiment, the processor is configured to predict the risk of the cardiac condition as one of:

a progression cardiac failure risk index determined by quantifying calculated cardiac index for apnoeic episodes over a time-period, or a future cardiac failure risk index determined based on prediction using calculated cardiac index for apnoeic episodes over a time-period.

In this regard, the term "progression cardiac failure risk index" refers to a quantitative measure that assesses a trend of cardiac function decline by analyzing the calculated cardiac index for the apnoeic episode(s) over a time-period. In this regard, the processor 102C continuously evaluates the cardiac index determined for each of the detected apnoeic episode and quantifies how the apnoeic episode varies over successive occurrences. It may be appreciated that data pertaining to cardiac index determined for apnoeic episode over a time period may be stored in the data repository as historical data for future analysis. Notably, if a progressive decrease in the cardiac index is observed over multiple apnoeic episodes, it may indicate worsening cardiac efficiency and an increased risk of the heart failure or any such cardiac condition. For example, if a patient or a person initially exhibits a cardiac index of 2.5 L/min/$m^2$, but over weeks or months this value declines below 2.2 L/min/$m^2$, the processor 102C identifies this downward trend and classifies the risk of cardiac condition accordingly.

Similarly, the "future cardiac failure risk index" refers to a predictive measure that estimates the likelihood of future cardiac failure based on the trend of the calculated cardiac index over a time-period. The processor 102C utilizes predictive modelling techniques, such as time-series analysis or machine learning algorithms, to extrapolate future values of the cardiac index based on past trends (can be derived from historical data pertaining to cardiac index, stored in the data repository). By leveraging historical cardiac index data from previous apnoeic episodes, the processor 102C generates a forecasted trajectory, estimating whether the cardiac index is likely to fall below the critical threshold of 2.2 L/min/$m^2$ in upcoming apnoeic episodes. For instance, if a patient's cardiac index exhibits a steady decline from 2.6 L/min/$m^2$ to 2.3 L/min/$m^2$ over consecutive apnoeic episodes, the processor 102C may predict that within a specific timeframe, the cardiac index may drop below 2.2 L/min/$m^2$, triggering an alert for potential future cardiac failure. The technical advantage is prediction of potential cardiac risk for the user, for ease of alert generation and administering healthcare provision.

In an embodiment, the processor is configured to generate an alert when any of the current cardiac failure risk index, the progression cardiac failure risk index or the future cardiac failure risk index exceeds a predetermined threshold. The alert serves as a proactive notification mechanism, enabling timely intervention when the cardiac function deteriorates beyond clinically significant limits. In this regard, the term "predetermined threshold" refers to a clinically defined value beyond which the cardiac failure risk is considered critical and requires immediate medical attention. Notably, the predetermined thresholds may be defined based on established medical guidelines or dynamically adjusted based on user-specific parameters such as physiological features of the user. For example, if the current cardiac failure risk index drops below 2.2 L/min/$m^2$, the processor 102C triggers an alert, signalling a state of potential cardiac insufficiency. It may be appreciated that based on current cardiac failure risk index, the progression cardiac failure risk index or the future cardiac failure risk index data collected over a time period, from a plurality of user subjected to clinical assessment may also be used to determine such predefined thresholds.

For the progression cardiac failure risk index, the alert is generated when a downward trend in the calculated cardiac index over multiple apnoeic episodes exceeds a critical rate of decline, indicating worsening the cardiac function. For instance, if the processor 102C detects that the calculated cardiac index is steadily decreasing over time and is projected to reach a critical level, it generates an early warning to notify clinicians and/or the user of potential heart failure progression. Similarly, for the future cardiac failure risk index, the processor 102C generates an alert if the predicted cardiac index falls below the predetermined threshold within an estimated future time frame. For example, if time-series analysis predicts that the calculated cardiac index will fall below 2.2 L/min/$m^2$ in the next three weeks, an alert is generated to prompt pre-emptive medical action. By continuously monitoring these risk indices, the processor 102C ensures that alerts are triggered at clinically relevant moments, preventing delayed diagnosis and enabling early medical intervention. The alerts may be a visual (dashboard notifications), an auditory (alarm signals), or wireless notifications (sent to healthcare providers via mobile applications or cloud-based platforms). This real-time risk assessment and alert mechanism provide enhanced patient safety, reducing the risk of cardiac failure progression and improving clinical outcomes through timely intervention. The technical advantage is reliable alert generation to promote early care to minimize cardiac risk in the user.

In an embodiment, the processor is further configured to determine the compensatory mechanical output using the filtered ECG data by:

- segmenting the ECG data into apnoeic period and non-apnoeic period;
- calculating ultra-short-term heart rate variability (HRV) during the apnoeic period and non-apnoeic period;
- identifying a reduction in ultra-short-term HRV during the apnoeic period and non-apnoeic period; and
- correlating the reduced ultra-short-term HRV with cardiac stress levels to determine the compensatory mechanical output.

Herein, the processor 102C is configured to segment the ECG data into apnoeic periods and non-apnoeic periods. In this regard, the term "apnoeic period" refers to a duration of the apnoeic episode while the user sleeps, during which respiratory signals are absent or significantly reduced, indicating a lack of breathing. Conversely, the term "non-apnoeic period" refers to a time duration where normal breathing patterns are observed and there is no sign of the apnoeic sleep. The processor 102C identifies the apnoeic and the non-apnoeic periods by synchronizing the ECG data with respiratory signals obtained from the BCG data. The technical advantage of segmenting the ECG data is that by segmenting the ECG data targeted data analysis can be performed on the BCG data (by corelating the segmented data and identifying time points of apnoeic episodes) and therefore improved clinical insights can be obtained.

Further, the processor 102C calculates ultra-short-term heart rate variability (HRV) during the apnoeic period and non-apnoeic period. Notably, the term "heart rate variability (HRI)" refers to the fluctuation in time intervals between consecutive heartbeats, which reflects an autonomic nervous system's regulation of cardiac activity. In this context, the ultra-short-term HRV is derived from short segments of the ECG data, typically captured in a time duration ranging from 5 seconds to 15 seconds, allowing real-time monitoring of even a small change in the heart rate dynamics that occurs during the apnoeic episode. Capturing of such small change aids in finding out relevant information on heart's condition and efficiency which ultimately aids in determining cardiac condition and associated risk.

In this regard, during severe sleep apnoea, the heart rate (HR) may decelerate markedly during apnoeic episodes due to hypoxia-induce parasympathetic dominance, followed by abrupt accelerations upon arousal and resumption of breathing (i.e., HR drops and then rises again once breathing resumes). Such cyclical pattern can lead to elevated global HRV metrics, which may paradoxically mask the presence or severity of sleep apnoea and its associated cardiovascular risks. In other words, the HRV may appear elevated due to shifts between apnoeic and non-apnoeic heart rates which may mask the presence of reduced adaptability of the autonomic nervous system, often pointing to heightened physiological or pathological stress. By segmenting the HRV data in ultra-short term time frames/windows (for example, 5 to 15 sec time frames) aligned with apnoeic and non-apnoeic periods and calculating ultra-short-term HRV for both apnoeic and non-apnoeic periods, distinct autonomic patterns or event-specific HRV biomarkers in the HRV data can be identified/extracted. Notably, such patterns/biomarkers can be corelated to possible cardiac conditions associated with apnoeic episodes.

Moreover, such segmentation (i.e., generating ultra-short-term HRV) enhances the detection of transient sympathetic surges and vagal withdrawals, offering finer temporal resolution for identifying physiological stress linked to apnoeic events. Notably, by identifying physiological stress linked to apnoeic events, clinically relevant insights into autonomic dysfunction and cardiovascular strain in patients with obstructive sleep apnoea, can be extracted. The technical advantage is that by calculating ultra-short-term HRV for both apnoeic and non-apnoeic periods, clinically relevant insights on cardiac conditions associated with apnoeic episodes can be easily identified and extracted.

The processor 102C applies time-domain HRV analysis techniques, such as Poincaré Plot plotted for standard deviation (SD1), RMSSD (Root Mean Square of Successive Differences), non-linear analysis technique such as symbolic dynamics analysis, beat-to-beat delta R-R analysis, to quantify cardiac variability. Notably, the term "R-R" refers to time frame between two successive R-waves (a tall, sharp spike in ECG data that represents the ventricular depolarization i.e., when the heart's ventricles contract). It may be appreciated that the processor 102C is configured to implement a machine-learning model to analyze the ultra-short term HRV to extract information on cardiac stress levels, the compensatory mechanical output and possible cardiac conditions.

The processor 102C further identifies a reduction in the ultra-short-term HRV during the apnoeic period and non-apnoeic period. A reduction in ultra-short-term HRV indicates a dominance of sympathetic nervous system activity, suggesting heightened cardiac stress and reduced parasympathetic regulation. Parasympathetic regulation reduction is particularly significant as normal HRV fluctuations are crucial for maintaining cardiovascular adaptability. When a reduction in ultra-short-term HRV is observed, it can indicate risk of cardiac stress. Reduced HRV is a recognized indicator of increased physiological stress on the heart. HRV reflects a shift in autonomic balance, typically marked by reduced parasympathetic (vagal) activity and heightened sympathetic activity. Such imbalance (i.e., between the parasympathetic and sympathetic activity) suggests that the cardiovascular system (specifically the heart) is under strain and has become less capable (compared to a healthy heart) of adapting to internal or external demands. Notably, persistently low HRV has been linked to increased resting HR, elevated blood pressure variability, and diminished baroreflex sensitivity. These metrics (i.e., increased resting HR, elevated blood pressure variability, and diminished baroreflex sensitivity) are essential identifiers of greater cardiac workload and stress. Clinically, reduced HRV is associated with higher risk and poor outcomes in conditions such as heart failure, myocardial infarction, and sleep apnoea. Even in healthy individuals, consistently low HRV (i.e., when low HRV is observed for a prolonged time period) may indicate inadequate recovery, chronic stress, or a higher risk for future cardiovascular events. Therefore, reduced HRV serves as a non-invasive, dynamic marker/identifier of the heart's regulatory capacity and its resilience under stress.

The processor 102C further correlates the reduced ultra-short-term HRV with cardiac stress levels to determine the compensatory mechanical output. In this regard, from the ultra-short-term HRV analysis hidden patterns tied to cardiac stress during apnoeic episode can be identified. By corelating these hidden patterns with indicators of cardiac stress such as stroke volume, the processor 102C can estimate how the heart is mechanically compensating and if there is any abnormality or anomaly in the activities of heart. The technical advantage is accurate analysis of heart signal to determine cardiac condition and associated risk.

In an embodiment, the processor is configured to detect the apnoeic episode as:

central sleep apnoea based on the absence of respiratory signals and normal intrathoracic pressure derived from BCG data during the apnoeic episode; and obstructive sleep apnoea based on the presence of respiratory signals and fluctuating intrathoracic pressure derived from BCG data during the apnoeic episode.

In this regard, the central sleep apnoea (CSA) is characterized by a temporary cessation of respiratory effort due to a failure in the brain's respiratory control centres. The absence of respiratory signals indicates that no airflow is detected, and the BCG-derived intrathoracic pressure remains stable, suggesting that the diaphragm and other respiratory muscles are not attempting to breathe. This lack of effort differentiates CSA from other forms of sleep apnoea, as the CSA signifies neurological suppression of respiration rather than airway obstruction. Conversely, in this regard, obstructive sleep apnoea (OSA) is caused by a physical blockage of upper airway, which prevents effective breathing despite continued respiratory effort. The presence of respiratory signals in the BCG data suggests that the body is attempting to breathe, but airflow is restricted due to airway collapse. Simultaneously, fluctuating intrathoracic pressure indicates increased respiratory effort, as the chest and diaphragm generate negative pressure in an attempt to overcome the obstruction. These fluctuations serve as a key marker of the OSA and differentiate it from the CSA. In this way, by leveraging the BCG data and the intrathoracic pressure dynamics, the processor 102C may accurately classifies the apnoeic episodes as either the CSA or the OSA. The technical advantage is providing useful information related to user's physiological state which may affect cardiac condition or may trigger any other possible health condition of the user.

Additionally, the processor 102C is configured to detect abnormal intrathoracic pressure fluctuations i.e., heart preload and heart afterload, in obstructive sleep apnoea by analyzing changes in the preload and afterload conditions of the heart as reflected in alterations of the BCG data (as signal morphology i.e., shape of waveform), specifically in the amplitude and timing relationships between the H, I, J, and K waves of the BCG signal. The detected abnormal thoracic pressure fluctuation can be corelated to apnoeic episodes. Notably, the term heart preload refers to the pressure on the heart muscle at the end of diastole. The term heart afterload is the pressure on the heart muscle must overcome to eject blood during start of systole.

In an embodiment, the wearable device further comprising a photoplethysmography (PPG) sensor operatively connected to the processor, wherein the processor is configured to identify timepoints in the heart signals of the filtered BCG data from a signal obtained from the PPG sensor.

In this regard, the signal obtained from PPG sensor is used to identify time points which can be correlated to apnoeic episodes. The term "time points" refers to starting and ending time which are related to start of drop in blood flow volume indicating start of apnoeic episode and end of apnoeic episode respectively. In this regard, the PPG sensor is a non-invasive optical sensor that detects fluctuations in blood flow volume by analyzing absorption and reflection of light in the blood vessels beneath the skin. Based on the analysis the processor 102C measures duration of apnoeic episode. Notably, during the apnoeic episode, the cessation or reduction of airflow leads to lowered cardiac output and a decline blood flow volume, which is captured by the PPG sensor. Additionally, PPG waveform (i.e., output from PGP sensor) is used to identify important time points relevant to the cardiac cycle and analysis of the cardiac waveform (i.e., heart signals) morphology, starting and ending of systole-diastole, any other changes in cardiac waveform, etc.

For example, in patients with sleep-disordered breathing or sleep apnoea, reduced airflow and blood flow volume may result in drop in blood oxygen levels below 90% and may pose a potential risk on cardiovascular system of body. Therefore, the data on blood flow volume is utilized to determine the time points of apnoeic episodes. From this data, starting and ending of apnoeic episodes and such details can be identified. The technical advantage is accurate determination of duration of apnoeic episode.

In this regard, the processor 102C is configured to continuously analyze PPG-derived timepoints and identify apnoeic episode resulted from respiratory distress. The detection of the apnoeic episode is enhanced by correlating the obtained timepoints with respiratory signals derived from BCG data to it determine duration of the apnoeic episode. Additionally, the signal obtained from the PPG sensor can provide insight into type of apnoeic episode. For example, if the signal amplitude reduces and when such drop is accompanied by fluctuating intrathoracic pressure signals, it may indicate obstructive sleep apnoea (OSA) where the airway is blocked but respiratory effort persists. If the signal amplitude 2 declines and the intrathoracic pressure remains stable, it may suggest central sleep apnoea (CSA), where breathing effort itself is absent due to neurological control failure. The technical advantage is that reliable information on user's health can be obtained.

It may be appreciated that the PPG waveform (specifically the peaks and dicrotic notch observed in morphology of the PPG waveform) aids to identify start, end, and other timepoints (from I, J, K, L-waveforms) of a single heartbeat from the received BCG data easily. Technical advantage is that by including PPG signal, identifying timepoints becomes simpler and more robust.

It may be further appreciated that the integration of PPG-based blood flow volume monitoring with BCG-derived respiratory signal analysis enables more accurate detection of the apnoeic episode, as a drop in blood flow volume (resulting decline in blood oxygen saturation) alone may not always be conclusive evidence of the apnoeic episode. For example, external factors such as movement artifacts or poor sensor contact can temporarily affect blood flow volume 2 readings. However, by correlating blood flow volume 2 drops with real-time respiratory patterns derived from the BCG sensor 102A, the wearable device 100 ensures that detected events are physiologically significant rather than caused by sensor errors or temporary signal fluctuations.

In an embodiment, the aforementioned wearable device further comprising an inertial measurement unit (IMU)

operatively connected to the processor and configured to determine a sleeping posture of a user, wherein the processor is configured to suggest an optimal sleeping posture by correlating the detected apnoeic episodes with the determined sleeping posture, wherein the optimal sleeping posture is identified based on a reduced occurrence of apnoeic episodes. In this regard, the inertial measurement unit (IMU) comprises sensors such as an accelerometer, gyroscope, and magnetometer, which collectively track the orientation, movement, and angular velocity of the wearable device 100. The accelerometer measures linear acceleration, allowing detection of changes in body position, while the gyroscope detects rotational movements, helping to determine shifts in sleeping posture. The magnetometer assists in spatial orientation by detecting earth's magnetic field. Notably, by continuously capturing motion data, the IMU enables precise classification of sleep positions, ensuring accurate correlation between body posture and apnoeic episodes. It may be appreciated that the processor 102C analyses posture data from the IMU to classify the user's sleeping position, such as supine, prone, or lateral. Notably, certain sleeping positions, such as the supine position, may contribute to airway obstruction, leading to increased frequency of apnoeic episodes, whereas other positions, such as lateral sleeping, may help reduce their occurrence. Herein, the processor 102C correlates the detected apnoeic episodes with the corresponding sleeping posture and identifies the posture in which apnoeic episodes occur less frequently or with reduced severity. Based on this correlation, the processor 102C determines the optimal sleeping posture and suggests positional adjustments to minimize apnoeic episodes. For example, if the wearable device 100 detects a higher occurrence of apnoeic episodes in the supine position, it may recommend the user to adopt a lateral sleeping position. The technical advantage is providing user with suitable medical advice to reduce apnoeic episodes.

The present disclosure also relates to a system for monitoring cardiac function during an apnoeic episode. It may be appreciated that various embodiments and variants disclosed above, with respect to the aforementioned wearable device 100, apply mutatis mutandis to the system as well.

Figure 3:
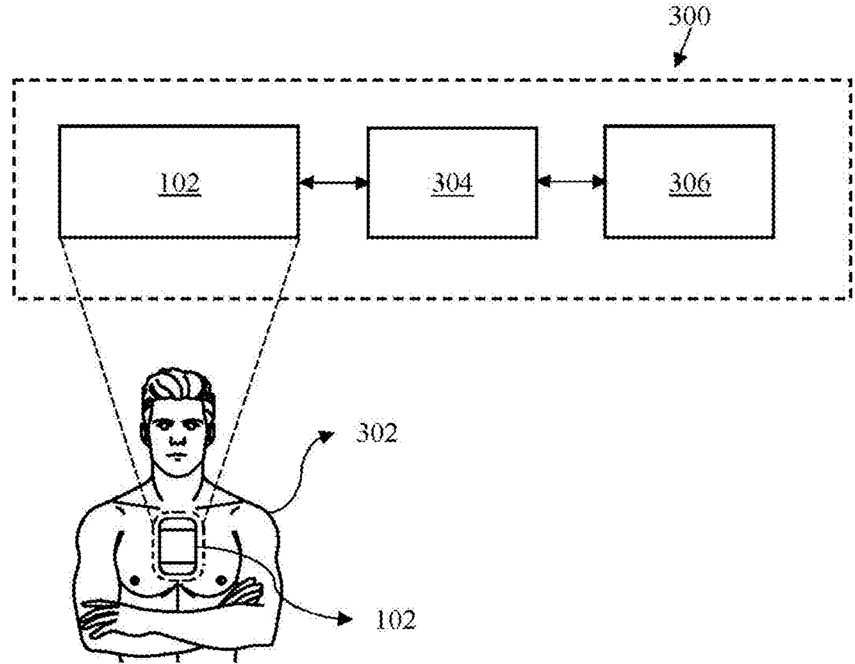
FIG. 3 illustrates an exemplary implementation of a system for monitoring cardiac function during an apnoeic episode, in accordance with an embodiment of the present disclosure.

Referring to FIG. 3, illustrated is an exemplary implementation of a system 300 for monitoring cardiac function during an apnoeic episode, in accordance with an embodiment of the present disclosure. As depicted in FIG. 3, the system 300 includes wearable device 100 configured to be worn on a chest near a sternum of a user 302. Notably, the wearable device 100 used in the system 300 is same as the wearable device 102 of FIGS. 1 and 2 which comprises the BCG sensor 102A, the ECG sensor 102B, and the processor 102C (not shown in FIG. 3). The system 300 also includes a server arrangement 304 communicably coupled to the wearable device 100 for receiving the BCG data and the ECG data. In this regard, the term "server arrangement" refers to at least one server communicably coupled to the wearable device 100 via a wired or a wireless connection (via a suitable network) and is designed to manage, store, and process data (i.e., both BCG data and ECG data, and derived data thereof) efficiently within the system. Notably, the server arrangement may be single server arrangement, client-based server arrangement, multi-tier architecture-based server arrangement, distributed server arrangement, clustered server arrangement, load-balanced server arrangement and so on. The server arrangement 304 is configured to filter respiratory signals and heart signals from the BCG data to extract relevant waveform components for further analysis. Moreover, the server arrangement 304 is configured to detect the apnoeic episode based on low respiratory signals or absence of respiratory signals for a predetermined time period in the filtered BCG data. In this regard, the term "predetermined time period" refers to a fixed duration of time set as a threshold to identify specific events, such as the apnoeic episode. For example, the predetermined time period is typically set based on clinical apnoea thresholds, such as at least 10 seconds of interrupted breathing, to distinguish between normal respiratory variations and pathological apnoeic events. By continuously monitoring BCG-derived respiratory waveforms, the server arrangement 304 can accurately identify the apnoeic episodes, enabling real-time detection and analysis of breathing irregularities. In this regard, the term "server arrangement" refers to a computational infrastructure, including one or more processing units, storage components, and communication interfaces, designed to process, analyze, and store physiological data received from the wearable device 100. The server arrangement 304 may be implemented as a cloud-based system, an on-premise computing unit, or a distributed processing network, facilitating real-time monitoring and assessment of cardiac health. The server arrangement 304 may execute various algorithmic functions, such as signal filtering, feature extraction, machine learning-based pattern recognition, and alert generation.

Further, the server arrangement 304 is configured to determine a compensatory mechanical output of the heart using at least one of the filtered BCG data or ECG data for the apnoeic episode. When the apnoeic event occurs, the heart often undergoes compensatory changes to counteract oxygen deprivation. The server arrangement 304 examines variations in the peak-to-peak amplitude changes in BCG signals, which correspond to changes in the stroke volume, as well as the heart rate fluctuations derived from the ECG data. By correlating these parameters, the system 300 determines how the heart adapts during the apnoeic episode, providing insight into the physiological strain imposed on the cardiovascular system.

Furthermore, the server arrangement 304 is configured to predict a risk of a cardiac condition based on the compensatory mechanical output during the apnoeic episode. The server arrangement 304 processes data from the filtered BCG data and ECG data to evaluate key cardiac performance indicators, such as stroke volume, cardiac output, and heart rate variability (HRV). Notably, the system 300 identifies anomalies or deviations in these parameters that may indicate an increased risk of cardiac conditions, such as heart failure, or cardiac stress. For example, if the cardiac index (cardiac output adjusted for body surface area) drops below the threshold of 2.2 L/min/$m^2$, it may indicate inadequate cardiac function, triggering an alert for the potential cardiac failure.

Notably, the system 300 also comprises a communication interface 306 such as a monitor, or a tablet where the data from the system 300 can be communicated to a healthcare authority (such as a doctor, a health care professional and so on), and via which the system 300 can receive commands and operational inputs when required.

In an embodiment, the server arrangement comprises an edge computing device or a cloud server. Herein, the term "edge computing device" refers to a local processing unit that is positioned near the data source, such as a smart hub, a gateway device, or an on-premise server. The edge computing device is configured to process the BCG and the ECG data in real-time, reducing latency and ensuring faster detection of apnoeic episodes and cardiac anomalies. For instance, in scenarios where instant alert generation is critical, such as detecting a significant drop in cardiac output during sleep, an edge computing device ensures that alerts are triggered immediately without relying on external network connectivity.

On the other hand, the cloud server provides remote storage, high-computational capacity, and large-scale data analytics. the cloud server facilitates for long-term tracking of physiological parameters, enabling comparative analysis over extended periods to detect progressive cardiac deterioration. For example, historical trends in cardiac index fluctuations across multiple apnoeic episodes can be analysed using advanced machine learning models deployed on the cloud. The cloud server also supports secure remote access, allowing healthcare professionals to review patient data and provide timely interventions. Notably, the choice between the edge computing and the cloud servers depends on specific use-case requirements, such as real-time responsiveness, computational demand, and data privacy considerations. In some implementations, a hybrid approach may be employed, where the edge computing device handles immediate processing, while the cloud server manages long-term data storage and advanced predictive analytics for enhanced cardiac health monitoring.

The present disclosure also relates to a method for monitoring cardiac function during an apnoeic episode. It may be appreciated that various embodiments and variants disclosed above, with respect to the aforementioned wearable device 100, and system 300 apply mutatis mutandis to the method as well.

Optionally, the aforementioned method is implemented utilizing the aforementioned wearable device 100 and system 300. It may be appreciated that the method is executed by the processor 102C of the wearable device 100 and the server arrangement 304 of the system 300.

Figure 4:
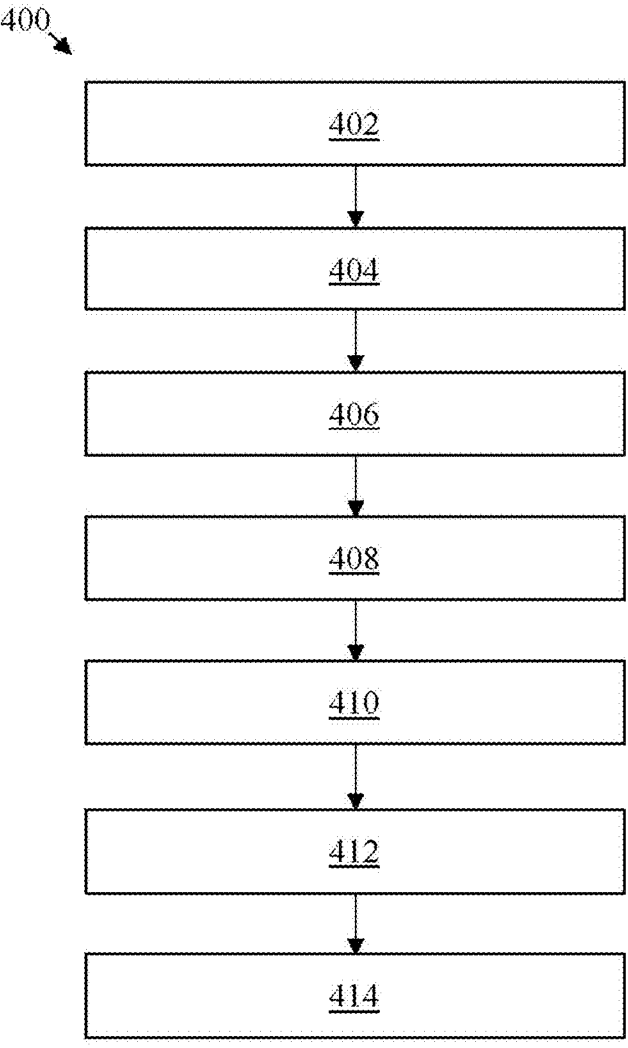
FIG. 4 illustrates a flow chart depicting steps of a method for monitoring cardiac function during an apnoeic episode, in accordance with an embodiment of the present disclosure.

Referring to FIG. 4, illustrated is a flow chart 400 depicting steps of a method for monitoring cardiac function during an apnoeic episode, in accordance with an embodiment of the present disclosure. The method include steps to monitor cardiac function during the apnoeic episode. At step 402, mechanical forces generated by a heart using a ballistocardiography (BCG) sensor is measured. At step 404, electrical activity of the heart using an electrocardiography sensor is measured. At step 406, BCG data from the measured mechanical forces and ECG data from the measured electrical activity are generated using a processor. At step 408, respiratory signals and heart signals are filtered from the BCG data. At step 410, the apnoeic episode is detected based on low respiratory signals or absence of respiratory signals for a predetermined time period in the filtered BCG data. At step 412, a compensatory mechanical output of the heart is determined using at least one of: the filtered BCG data or ECG data for the apnoeic episode. At step 414, a risk of a cardiac condition is predicted based on the compensatory mechanical output during the apnoeic episode.

In an embodiment, determining the compensatory mechanical output using the filtered BCG data comprise:

- determining a stroke volume by calculating area under curve between peaks of the heart signals of the filtered BCG data before, during, and after the apnoeic episode;
- identifying the stroke volume corresponding to increased peak-to-peak amplitude changes in the heart signals during the apnoeic episode; and
- calculating a cardiac output as a product of a heart rate determined from the ECG data after the apnoeic episode and the identified stroke volume after the apnoeic episode.

In an embodiment, predicting the risk of the cardiac condition comprises a current cardiac failure risk index, calculated using a cardiac index, which is the cardiac output adjusted for body surface area.

In an embodiment, predicting the risk of the cardiac condition further comprises:

- a progression cardiac failure risk index determined by quantifying the calculated cardiac index for apnoeic episodes over a time period; or
- a future cardiac failure risk index determined based on prediction using the calculated cardiac index for apnoeic episodes over a time period.

In an embodiment, the method further comprising generating an alert when any of the current cardiac failure risk index, the progression cardiac failure risk index, or the future cardiac failure risk index exceeds a predetermined threshold.

In an embodiment, determining the compensatory mechanical output using the filtered ECG data comprises:

- segmenting the ECG data into apnoeic period and non-apnoeic period;
- calculating ultra-short-term heart rate variability (HRV) during the apnoeic period and non-apnoeic period;
- identifying a reduction in ultra-short-term HRV during the apnoeic period and non-apnoeic period; and
- correlating the reduced ultra-short-term HRV with cardiac stress levels to determine the compensatory mechanical output.

In an embodiment, detecting the apnoeic episode comprises:

- detecting central sleep apnoea based on the absence of respiratory signals and relatively stable intrathoracic pressure derived from BCG data during the apnoeic episode, and
- detecting obstructive sleep apnoea based on the presence of respiratory signals and fluctuating intrathoracic pressure derived from BCG data during the apnoeic episode.

In an embodiment, the method further comprises identifying timepoints in the heart signals of the filtered BCG data from a signal obtained from a PPG sensor.

In an embodiment, the method further comprises:

- determining a sleeping posture of a user using an inertial measurement unit (IMU);
- correlating the detected apnoeic episodes with the determined sleeping posture; and
- identifying an optimal sleeping posture based on a reduced occurrence of apnoeic episodes.

The invention claimed is:

1. A wearable device comprising:

a ballistocardiography (BCG) sensor configured to measure mechanical forces generated by a heart and respiratory movement;

an electrocardiography (ECG) configured to measure electrical activity of the heart;

a processor operatively connected to the BCG sensor and the ECG sensor to generate BCG data from the mechanical forces and ECG data from the electrical activity, wherein the processor is configured to:

filter respiratory signals and heart signals from the BCG data;

determine that an apnoeic episode has occurred based on a respiratory signal amplitude derived from the filtered BCG data being below a predefined threshold for at least a predetermined duration;

for the apnoeic episode, determine a compensatory mechanical output of the heart using the ECG data by:

calculating ultra-short-term heart rate variability (HRV) from an ECG time segment corresponding to an apnoeic period and from an ECG time segment corresponding to a non-apnoeic period;

identifying a reduction in the ultra-short-term HRV during the apnoeic period relative to the non-apnoeic period; and correlating the identified reduction in the ultra-short-term HRV with cardiac stress indicators; and predict a risk of a cardiac condition based on the determined compensatory mechanical output during the apnoeic episode.

2. The wearable device according to claim 1, wherein the processor is further configured to determine the compensatory mechanical output using the filtered BCG data by:

determining a stroke volume by calculating area under curve between peaks of the heart signals of the filtered BCG data before, during and after the apnoeic episode, identifying the stroke volume corresponding to increased peak-to-peak amplitude changes in the heart signals during the apnoeic episode, and calculating a cardiac output as a product of a heart rate determined from the ECG data after the apnoeic episode and the identified stroke volume after the apnoeic episode.

3. The wearable device according to claim 2, wherein the processor is configured to predict the risk of the cardiac condition as a current cardiac failure risk-index, calculated using a cardiac index, which is the cardiac output adjusted for body surface area.

4. The wearable device according to claim 3, wherein the processor is configured to predict the risk of the cardiac condition as one of:

a progression cardiac failure risk index determined by quantifying calculated cardiac index for apnoeic episodes over a time-period, or a future cardiac failure risk index determined based on prediction using calculated cardiac index for apnoeic episodes over a time-period.

5. The wearable device according to claim 4, wherein the processor is configured to generate an alert when any of the current cardiac failure risk index, the progression cardiac failure risk index or the future cardiac failure risk index exceeds a predetermined threshold.

6. The wearable device according to claim 1, wherein the processor is configured to detect the apnoeic episode as:

central sleep apnoea based on the absence of respiratory signals and normal intrathoracic pressure derived from BCG data during the apnoeic episode; and obstructive sleep apnoea based on the presence of respiratory signals and fluctuating intrathoracic pressure derived from BCG data during the apnoeic episode.

7. The wearable device according to claim 1, further comprising a photoplethysmography (PPG) sensor operatively connected to the processor, wherein the processor is configured to identify timepoints in the heart signals of the filtered BCG data from a signal obtained from the PPG sensor.

8. The wearable device according to claim 1, further comprising an inertial measurement unit (IMU) operatively connected to the processor and configured to determine a sleeping posture of a user, wherein the processor is configured to suggest an optimal sleeping posture by correlating the detected apnoeic episodes with the determined sleeping posture, wherein the optimal sleeping posture is identified based on a reduced occurrence of apnoeic episodes.

9. The wearable device according to claim 1, wherein the ultra-short-term heart rate variability (HRV) is calculated from segments of the ECG data having a duration of 5 seconds to 15 seconds.

10. The wearable device according to claim 1, wherein the processor is configured to identify patterns in the ultra-short-term heart rate variability (HRV) during the apnoeic period and correlate the identified patterns with the cardiac stress indicators, wherein the cardiac stress indicators comprise at least one of heart rate variability (HRV), heart rate, stroke volume, cardiac output, cardiac index, blood pressure variability, or baroreflex sensitivity derived from the ECG data or the BCG data.

11. A system comprising:

a wearable device configured to be worn on a chest near a sternum of a user, the wearable device comprising:

a ballistocardiography (BCG) sensor configured to measure mechanical forces generated by a heart, an electrocardiography (ECG) configured to measure electrical activity of the heart, and a processor operatively connected to the BCG sensor and the ECG sensor to generate BCG data from the mechanical forces and ECG data from the electrical activity; and a server arrangement communicably coupled to the wearable device for receiving the BCG data and the ECG data, the server arrangement is configured to:

filter respiratory signals and heart signals from the BCG data;

determine that an apnoeic episode has occurred based on a respiratory signal amplitude derived from the filtered BCG data being below a predefined threshold for at least a predetermined duration;

for the apnoeic episode, determine a compensatory mechanical output of the heart using the ECG data by:

calculating ultra-short-term heart rate variability (HRV) from an ECG time segment corresponding to an apnoeic period and from an ECG time segment corresponding to a non-apnoeic period;

identifying a reduction in HRV during the apnoeic period relative to the non-apnoeic period; and correlating the identified reduction in the ultra-short-term HRV with cardiac stress indicators; and predict a risk of a cardiac condition based on the determined compensatory mechanical output during the apnoeic episode.

12. The system according to claim 11, wherein the server arrangement comprises an edge computing device or a cloud server.

13. A method comprising:

measuring mechanical forces generated by a heart using a ballistocardiography (BCG) sensor;

measuring electrical activity of the heart using an electrocardiography (ECG) sensor;

generating BCG data from the mechanical forces and ECG data from the electrical activity using a processor;

filtering respiratory signals and heart signals from the BCG data;

determining that an apnoeic episode has occurred based on a respiratory signal amplitude derived from the filtered BCG data being below a predefined threshold for at least a predetermined duration;

for the apnoeic episode, determining a compensatory mechanical output of the heart using the ECG data by:

calculating ultra-short-term heart rate variability (HRV) from an ECG time segment corresponding to an apnoeic period and from an ECG time segment corresponding to a non-apnoeic period;

identifying a reduction in the ultra-short-term HRV during the apnoeic period relative to the non-apnoeic period; and correlating the identified reduction in the ultra-short-term HRV with cardiac stress indicators; and predicting a risk of a cardiac condition based on the determined compensatory mechanical output during the apnoeic episode.

14. The method according to claim 13, wherein the method further comprises determining the compensatory mechanical output using the filtered BCG data comprise:

determining a stroke volume by calculating area under curve between peaks of the heart signals of the filtered BCG data before, during, and after the apnoeic episode;

identifying the stroke volume corresponding to increased peak-to-peak amplitude changes in the heart signals during the apnoeic episode; and calculating a cardiac output as a product of a heart rate determined from the ECG data after the apnoeic episode and the identified stroke volume after the apnoeic episode.

15. The method according to claim 14, wherein predicting the risk of the cardiac condition comprises a current cardiac failure risk index, calculated using a cardiac index, which is the cardiac output adjusted for body surface area.

16. The method according to claim 15, wherein predicting the risk of the cardiac condition further comprises:

a progression cardiac failure risk index determined by quantifying the calculated cardiac index for apnoeic episodes over a time period; or a future cardiac failure risk index determined based on prediction using the calculated cardiac index for apnoeic episodes over a time period.

17. The method according to claim 16, further comprising generating an alert when any of the current cardiac failure risk index, the progression cardiac failure risk index, or the future cardiac failure risk index exceeds a predetermined threshold.

18. The method according to claim 13, wherein detecting the apnoeic episode comprises:

detecting central sleep apnoea based on the absence of respiratory signals and relatively stable intrathoracic pressure derived from BCG data during the apnoeic episode, and detecting obstructive sleep apnoea based on the presence of respiratory signals and fluctuating intrathoracic pressure derived from BCG data during the apnoeic episode.

19. The method according to claim 13, further comprising:

determining a sleeping posture of a user using an inertial measurement unit (IMU);

correlating the detected apnoeic episodes with the determined sleeping posture; and identifying an optimal sleeping posture based on a reduced occurrence of apnoeic episodes.

20. The method according to claim 13, wherein the ultra-short-term heart rate variability (HRV) is calculated from segments of the ECG data having a duration of 5 seconds to 15 seconds.

* * * * *